United States Patent [19]
Tsien et al.

[11] Patent Number: 6,031,094
[45] Date of Patent: Feb. 29, 2000

[54] BETA-LACTAM SUBSTRATES AND USES THEREOF

[75] Inventors: Roger Y. Tsien, La Jolla; Gregor Zlokarnik, San Diego, both of Calif.

[73] Assignee: The Regents of the University of California, Oakland, Calif.

[21] Appl. No.: 09/128,679

[22] Filed: Jul. 23, 1998

[51] Int. Cl.[7] .................... C07D 205/085; C07D 205/08
[52] U.S. Cl. ........................... 540/363; 540/364; 435/18; 435/19
[58] Field of Search .................. 540/363, 364; 435/18, 19

[56] References Cited

U.S. PATENT DOCUMENTS

| | | | |
|---|---|---|---|
| 4,234,683 | 11/1980 | McMillan | 435/18 |
| 4,383,032 | 5/1983 | Stahl et al. | 435/23 |
| 4,448,880 | 5/1984 | Schindler et al. | 435/18 |
| 4,740,459 | 4/1988 | Chen et al. | 435/18 |
| 4,760,018 | 7/1988 | Charm | 435/7 |
| 4,764,462 | 8/1988 | Bredehorst et al. | 435/18 |
| 4,978,613 | 12/1990 | Bieniarz et al. | 435/18 |
| 5,162,524 | 11/1992 | Farina et al. | 540/358 |
| 5,264,346 | 11/1993 | Chen | 435/25 |
| 5,338,843 | 8/1994 | Quante et al. | 540/222 |
| 5,501,979 | 3/1996 | Gellar et al. | 435/320.1 |
| 5,514,561 | 5/1996 | Quante et al. | 435/18 |
| 5,583,217 | 12/1996 | Quante et al. | 540/225 |
| 5,593,866 | 1/1997 | Hancock et al. | 435/69.7 |
| 5,631,139 | 5/1997 | Wong et al. | 435/18 |
| 5,639,596 | 6/1997 | Bornkamm et al. | 435/5 |
| 5,741,657 | 4/1998 | Tsien et al. | 435/18 |

FOREIGN PATENT DOCUMENTS

| | | |
|---|---|---|
| 0 053 541 A1 | 6/1982 | European Pat. Off. . |
| 0 354 757 A2 | 1/1990 | European Pat. Off. . |
| WO 96/30540 | 10/1996 | WIPO . |
| WO 98/13353 | 4/1998 | WIPO . |

OTHER PUBLICATIONS

Zrihen et al, Eur. J. Med. Chem., Chim. Ther., 18(4), 1983.
Wakselman et al, Chem. Lett., (3), pp. 333–336, 1982.
Alam et al., Analyt. Biochem. 188:245–254 (1990).
Ambler R.P., Phil. Trans. R. Soc. Lond. B. 289:321–331 (1980).
Bulychev, J.A.C.S. 117:5938 (1995).
Bojarski et al., "Energy transfer and Migration in Fluorescent Solutions", Photochem. And Photophysics, edited by Rabeck, J.F. Boca Raton: CRC Press, Inc. 1990, pp. 1–57.
Bundgaard, "Design ofProdrugs: Bioreversible derivatives for various functional groups and chemical entities",Elsevier Science Publishers (1985).
Bunnell et al., "Industrial manufacture ofcephalosporius", Beta–Lactam Antibiotics fir Clinical Use. Series: Clinical Pharmacology vol. 4, edited by Queener, S.F., Webber, J.A. and Queener, S.W., New York: M. Dekker, 1986, pp. 255–283.
Bush et al., Antimicrobial Agents and Chemotherapy. pp.06–10 (1984).
Cartwright et al., Yeast. 10:497–508 (1994).
Castagnoli et al., Genet. Res. 40:217–231 (1982).
Castelli et al., Gene. 142:113–117 (1994).
Chang et al., P.N.A.S. 87:2823–2827 (1990).
Christensen et al., Biochem. J. 266:853–861 (1990).
Cuchural et al., J. Antimicrobial Chemother. 22:785–790, 1988.
De Sutter et al., Mol. Immul. 31:261–267 (1994).
Dos Remedios et al., J. Muscle Res. And Cell. Motility. 8:97–117, 1987.
Ferres H., "Pro–drugs of B–Lactamase antibiotics", Chem. Ind. pp. 435–440 (1980).
Forster, Annalen. Der Physik. G. Folge. Band. 2.:55–75 (1948).
Garcia et al., J. Biol. Chem. 262:9463–9468 (1987).
Gorman et al., Mol. Cell. Biol. 2:1044–1051 (1982).
Jansen et al., J. Chem. Soc. pp. 2127–2132 (1965).
Jones et al., J. Clin. Microbiol. 15:677–683 (1982).
Kadonga et al., J. Biol. Chem. 259:2149–2154, 1984.
Knowles, Acc. Chem. Res. 18:97–104 (1985).
Kuo et al., Analyt. Biochem. 177:165–167 (1989).
Lakowicz, Methods in Cell Biology. vol. 30., pp. 304–339, 1983.
Molecular Probes, Product Information Sheet. pp. 1–4 (1997).
Moore et al., Analyt. Biochem. 247:203–209 (1997).
Murphy et al., Biochem. 30:3640–3649 (1991).
O'Callaghan et al., Antimicrobial Agents and Chemotherapy. pp. 57–63 (1968).
O'Callaghan et al., Antimicrob. Agents Chemotherapy. 1:283–288 (1972).
Page, M.I., "The Mechanisms of Reactions of B–Lactam Antibiotics", Adv. Phys. Org. Chem. 23:165–270 (1987).

(List continued on next page.)

*Primary Examiner*—Ba K. Trinh
*Attorney, Agent, or Firm*—Gray Cary Ware & Freidenrich LLP; Lisa A. Haile

[57] ABSTRACT

Formula 1:

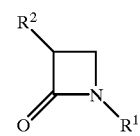

Substrates for beta-lactamase of general formula 1, in which $R^1$ is a moiety, in which a primary amine attached to an aryl carbon of a fluorophore precursor was converted into the nitrogen atom of the beta-lactam ring and the fluorophore precursor is not anthranilic acid when $R^2$ is H; $R^2$ is selected from the group consisting of H and $-NR^3R^4$, in which $R^3$ and $R^4$ are selected from the group consisting of H, aliphatic, alkyl, and acyl; and the beta-lactam ring may be cleaved by a beta-lactamase enzyme. Methods of assaying beta-lactamase activity and monitoring expression in systems using beta-lactamase as a reporter gene are also disclosed.

27 Claims, No Drawings

OTHER PUBLICATIONS

Parr et al., Antimicrobial Agents Chemother. 31:121–123, 1987.
Pratt et al., P.N.A.S. 81:1302–1306 (1984).
Richmond et al., Ann N.Y. Sci., 182:243–257 (1971).
Richmond et al., Adv. Microb. Physiol. 9:31–88 (1973).
Rodrigues et al., Cancer Res. 55:63–70 (1995).
Rosenthal et al., Meth. Enzymol. 152:704–720 (1987).
Sekkali et al., Mol. Marine Biol. Biotech. 3:30–34, 1994.
Shiau et al., Gene. 67:295–299 (1988).
Simon et al., J. Cell. Biol. 104:1165–1172 (1987).
Simonen et al., J. Biol. Chem. 269:13887–13892 (1994).
Stratton C.W., J. Antimicrobial Chemotherapy, pp. 23–35 (1988).
Stryer, "Introduction of Enzymes"Biochemistry. pp. 115–149 (1981).
Sutcliffe, P.N.A.S. 75:3737–3741 (1978).
Taylor et al., San Diego: Academic Press (1989) pp. 219–243.
Tsien et al., Handbook of BiologicalConfocal Microscopy, edited by James B. Pawley, Plenum Publishing Corp., pp. 169–178 (1990).
Tsien et al., "Practical design criteria for a dynamic ratio imaging system", Cell Calcium (1990) 11:93–109.
Turro, Menlo. Part: Benjamin/Cummings Publishing Co., Inc. pp. 296–361 (1978).
Van Heyningen et al., J. Med. Chem. 8:174–181 (1965).
Waterham et al., J. Cell. Biol. 127:737–749 (1994).
Wiedman et al., Nature. 309:637–639 (1984).
Wong et al., Gene. 10:87–94, 1980.
Wong, Gene. 83:215–223 (1989).
Yaron et al., Anal. Biochem. 95:228–235 (1979).
Young et al., Anal. Biochem. 215:24–30 (1993).

BETA-LACTAM SUBSTRATES AND USES THEREOF

TECHNICAL FIELD

The present invention relates generally to the fields of chemistry and biology. More particularly, the present invention relates to compounds that are substrates for beta-lactamase activity and methods for their use in measuring beta-lactamase activity.

BACKGROUND

A reporter gene assay measures the activity of a gene's promoter, and thus the expression of the proteins encoded by the gene or genes that are under the control of the promoter. These proteins can be involved in a variety of cellular activities. Therefore, a reporter gene assay also measures cellular activities associated with the proteins. These assays generally use techniques in molecular biology to make nucleic acid constructs that place a gene under the control of a promoter. These constructs can then be stably or transiently introduced into a cell, such as a mammalian cell (see, Gorman, C. M. et al,. Mol. Cell Biol. 2: 1044–1051 (1982); and Alam. J. and Cook, J. L., Anal.Biochem. 188: 245–254, (1990)). When the promoter is activated, the reporter gene is expressed and a reporter protein is produced. The reporter protein can be, for example, an enzyme that converts a substrate into a detectable product. The product can be measured qualitatively or quantitatively as a measure of the activation of the promoter and thus the level of activity of the genes normally under the control of that promoter.

Several reporter genes are known in the art and some are commercially available (see, Alam and Cook, supra). The reporter gene can be inserted within a plasmid that is particularly suited for an organism and molecular biology manipulations. Promoters of interest can be inserted into cloning sites so that the expression of the reporter gene is under the control of the promoter (see, Rosenthal, N., Methods Enzymol. 152: 704–720 (1987); and Shiau, A. and Smith, J. M., Gene 67: 295–299 (1988)). Known methods are used to introduce these plasmids into a cell type or whole organism (see, Sambrook et al., Molecular Biology, A Laboratory Manual, Cold Spring Harbor Laboratory Press (1989); and Nolan, In: Molecular Cloning, Cold Spring Harbor Laboratory Press, (1989)). The plasmids can also encode a resistance marker, such as resistance to antibiotics so that successfully transfected cells can be selected, identified, and cultured.

Substrates for enzymatic reporter proteins can be chromogenic or fluorescent. In some assays, a fluorescent substrate changes fluorescence properties upon conversion by the reporter enzyme to a fluorescent product. Preferably, a fluorescent product is highly fluorescent and can become trapped within the cell rather than being detectable in the media surrounding the cells. These features allow the expression of the reporter protein to be monitored and measured in individual cells rather than in a population of cells (see, WO 96/30540 to Tsien, published Oct. 3, 1996).

One way to increase the sensitivity of a fluorescent reporter assay is to maximize the amount of a fluorescent signal generated by a single reporter enzyme. An optimal enzyme will convert $10^5$ substrate molecules per second under saturating conditions (see, Stryer, L. Introduction to enzymes. In: Biochemistry, New York: W. H. Freeman and company, 1981, pp. 103–134). Beta-lactamases can cleave about $10^3$ molecules of a preferred substrates per second (see, Chang, Y. H. et al., Proc.Natl.Acad.Sci.USA 87: 2823–2827 (1990)). A preferred fluorescent product can produce up to $10^6$. In practice, a small fraction of the photons generated by the fluorescent product will be detected.

A preferred fluorescent substrate has a high turnover and optical properties such as high extinction and high fluorescence quantum yield. This present invention provides such preferred fluorescent substrates and provides additional benefits as well.

SUMMARY OF THE INVENTION

One object of the present invention is to provide compounds that are substrates for beta-lactamase that are suitable for use in a reporter gene assay. It is a further object of the invention to provide membrane-permeant compounds that can be transformed into substantially membrane-impermeant compounds after entry into a cell.

In accordance with the present invention, compounds are provided having the general formula 1:

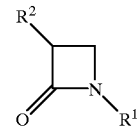

wherein:
  $R^1$ is a moiety, in which a primary amine attached to an aryl carbon of a fluorophore precursor was converted into the nitrogen atom of the beta-lactam ring and the fluorophore precursor is not anthralic acid when $R^2$ is H;
  $R^2$ is selected from the group consisting of H and $-NR^3R^4$, in which $R^3$ and $R^4$ are selected from the group consisting of H, aliphatic, alkyl, and acyl; and the beta-lactam ring may be cleaved by a beta-lactamase enzyme.

In another aspect of the present invention, if a compound having the general formula 1 contains a carboxyl group, the carboxyl group can be converted to an ester, or other derivative, which can produce a membrane-permeant derivative. The ester can be cleaved by endogenous mammalian intracellular esterases.

In another aspect of the present invention, if a compound having the general formula 1 contains a primary amine, the amino group can be converted to an acyl amine or other derivatives, which can produce a membrane-permeant derivative.

In another aspect of the present invention, compounds having the general formula 1 are prepared by reacting a fluorophore precursor having a primary amine attached to an aryl carbon with $XCH_2CHR^2COX''$ in the presence of a base, in which X and X'' are suitable leaving groups, $R^2$ is selected from the group consisting of H and $-NR^3R^4$, wherein $R^3$ and $R^4$ are selected from the group consisting of H, aliphatic, alkyl, and acyl.

In another aspect, the present invention provides a method for determining whether a beta-lactamase enzyme can cleave a compound of the present invention having the general formula 1, or a membrane permeant derivative thereof. The method involves contacting the sample with a compound of the present invention, exciting the sample with radiation of one or more wavelengths that are suitable for the cleaved compound, and determining the degree of fluorescence emitted from the sample. A degree of fluorescence emitted from the sample that is greater than an expected degree indicates that the beta-lactamase enzyme can cleave the compound and that the compound is a substrate for the beta-lactamase enzyme.

In another aspect, the present invention provides methods for determining whether a sample contains beta-lactamase activity. The method involves contacting the sample with a compound of the present invention, exciting the sample with radiation of one or more wavelengths that are suitable for the cleaved compound, and determining the degree of fluorescence emitted from the sample. A degree of fluorescence emitted from the sample that is greater than an expected degree indicates the presence of beta-lactamase activity in the sample. One aspect of this method is for determining the amount of an enzyme in a sample by determining the degree of fluorescence emitted at a first and second time after contacting the sample with a compound of the present invention. The difference in the degree of fluorescence emitted from the sample at the first and second time is determined. That difference reflects the amount of a beta-lactamase enzyme in the sample.

In another aspect, the present invention is directed to screening assays using the compounds of the present invention and a host cell, such as a mammalian cell, transfected with at least one recombinant nucleic acid molecule encoding at least one protein having beta-lactamase activity. Such recombinant nucleic acid molecule comprise expression control sequences adapted for function in a eukaryotic cell, such as a vertebrate cell, operatively linked to a nucleotide sequence coding for the expression of a beta-lactamase enzyme. The present invention also provides recombinant nucleic acid molecules comprising expression control sequences adapted for function in a eukaryotic cell, such as a vertebrate cell, operably linked to a nucleotide sequence coding for the expression of a cytosolic beta-lactamase enzyme.

In another aspect, the present invention provides methods for determining the amount of beta-lactamase activity in a cell. This method involves providing a sample comprising a host cell transfected with a recombinant nucleic acid molecule comprising a host cell having expression control sequences operatively linked to nucleic acid sequences coding for the expression of a beta-lactamase enzyme. The sample can comprise whole host cells, or an extract of the host cells, which is contacted with a compound of the present invention. The amount of compound cleaved is measured, whereby the amount of substrate cleaved is related to the amount of beta-lactamase activity in the host cell.

In another aspect, the present invention provides methods for monitoring the expression of a gene operably linked to a set of expression control sequences. The methods involve providing a host eukaryotic cell transfected with a recombinant nucleic acid molecule. The nucleic acid molecule comprises a set of expression control sequences operatively linked to nucleic acid sequences coding for the expression of a beta-lactamase enzyme, except if the host eukaryotic cell is a fungus, the beta-lactamase is a cytosolic beta-lactamase enzyme. A sample comprising the host eukaryotic cell, or an extract or conditioned medium produced therefrom or thereby, with a compound of the present invention. The amount of compound cleaved is determined using the methods of the present invention, wherein the amount of substrate cleaved is related to the amount of beta-lactamase activity in the host eukaryotic cell, which is related to the expression of the gene.

In another aspect, the present invention provides methods for determining whether a test compound alters the expression of a gene operably linked to a set of expression control sequences. The methods involve providing a host eukaryotic cell transfected with a recombinant nucleic acid construct. The recombinant nucleic acid construct comprises a set of expression control sequences operably linked to nucleic acid sequences coding for the expression of a beta-lactamase enzyme except if the host eukaryotic cell is a fungus, wherein the beta-lactamase is a cytosolic beta-lactamase enzyme. The host eukaryotic cell is contacted with the test compound. This host eukaryotic cell is then contacted with a compound of the present invention. The amount of the compound of the present invention cleaved is then measured using the methods of the present invention, whereby the amount of the compound of the present invention cleaved is related to the amount of beta-lactamase activity in the cell.

In another aspect, the present invention provides methods of clonal selection by providing cells transfected with a recombinant nucleic acid molecule comprising at least one expression control sequences operably linked to at least one nucleic acid sequence coding for the expression of a cytosolic beta-lactamase enzyme. The cells are contacted with a substance that activates, inhibits, or has no effect on the activation of the expression control sequence. The cells are contacted with a compound of the present invention. The amount of the compound of the present invention cleaved is determined within individual cells (including each individual cell), whereby the amount of the compound of the present invention cleaved reflects the amount of beta-lactamase activity in the cells. Cells having a selected level of beta-lactamase activity are selected and propagated.

Another aspect of the present invention is to use a beta-lactamase reporter gene and a compound of the present invention to screen test chemicals for biochemical activity within at least one cell comprising providing cells transfected with a recombinant nucleic acid molecule. The recombinant nucleic acid molecule comprises at least one expression control sequence operably linked to at least one nucleic acid sequence encoding for the expression of a beta-lactamase enzyme. The cells are contacted with a test chemical that may activate, inhibit, or have no effect on the activation of the expression control sequence. The cells are contacted with a compound of the present invention and the amount of the compound cleaved is measured. The amount of compound cleaved reflects the amount of beta-lactamase activity within the at least one cell, which reflects a biochemical activity within the at least one cell.

DESCRIPTION OF THE INVENTION

Definitions

In accordance with the present invention and as used herein, the following terms are defined with the following meanings, unless stated otherwise.

The term "dye" refers to a molecule or part of a compound that absorbs specific frequencies of light, including but not limited to ultraviolet light. The terms "dye" and "chromophore" are synonymous.

The term "fluorophore" refers to a chromophore that fluoresces.

The term "fluorophore precursor" refers to a molecule that has a chromophore that fluoresces and that has a primary amine attached to an aryl carbon.

The term "alkyl" refers to straight, branched, and cyclic aliphatic groups of 1 to 8 carbon atoms, preferably 1 to 6 carbon atoms, and most preferably 1 to 4 carbon atoms. The term "lower alkyl" refers to straight and branched chain alkyl groups of 1 to 4 carbon atoms.

The term "acyl" refers to —C(O)R', in which R' is a straight, branched, or cyclic aliphatic group of 1 to 8 carbon atoms, preferably 1 to 6 carbon atoms, and most preferably 1 to 4 carbon atoms.

The term "membrane-permeant derivative" means a chemical derivative of a compound of general formula 1, wherein any primary amine has been acylated or any carboxyl or —SO$_3$H moiety has been esterified. These derivatives are better able to cross cell membranes, i.e. membrane permeant, because hydrophilic groups are masked to provide more hydrophobic derivatives.

The term "aliphatic" refers to saturated and unsaturated alkyl groups of 1 to 10 carbon atoms, preferably 1 to 6 carbon atoms, and most preferably 1 to 4 carbon atoms.

The term "beta-lactamase enzyme" refers to an enzyme that can cleave a beta-lactam ring. Examples of a beta-lactamase enzyme include the naturally occurring forms of beta-lactamase and enzymes that have been prepared by mutagenesis of beta-lactamase enzymes. If a beta-lactamase enzyme can cleave the beta-lactam ring in particular compound having the general formula 1 (or its membrane permeant derivative), then this particular compound is a substrate of this invention for this particular beta-lactamase enzyme (see, for example, WO 96/30540, published Oct. 3, 1996).

The term "derivative" means a derivative of a compound that retains the underlying chemical structural of the original compound, or if the underlying structure has changed, can be readily converted into the original compound.

Compounds

Beta-lactamases cleave the beta-lactam ring of beta-lactam antibiotics, such as penicillins and cephalosporins, generating new charged moieties in the process (see, O'Callaghan, C. H. et al., Antimicrob.Agents.Chemother. 8: 57–63, (1968); and Stratton, C. W., J. Antimicrob. Chemother. 22, Suppl. A: 23–35 (1988)). A 1-aryl-beta-lactam is illustrated below, with the arrow pointing to the site of cleavage by a beta-lactamase enzyme. Cleavage of this compound by beta-lactamase produces a propionic acid functionality attached to the aryl amine, and at physiological pH, this cleaved compound has an additional negative charge because of the acid functionality.

There are a number of synthetic routes for the formation of beta-lactam ring systems (see, Heusler, In: Cephalosporins and Penicillins: Chemistry and Biology, ed Flynn, Academic Press, New York., pp. 255–280 (1972); Sammes, Chem. Reviews 76:113–155 (1976); Cooper, In topics in Antibiotic Chemistry. Vol. 3, ed. Sammes et al., Ellis Horwood, Ltd, Chichester, U. K., pp. 39–199 (1980); Jung et al., Topics in Antibiotic Chemistry, Vol. 4, Ellis Horwood, Ltd. Chichester, U. K., pp. 11–241 (1980); Ernest, In: Chemistry and biology of Beta-Lactam Antibiotics, Vol. 2. Nontraditional Beta-Lactam Antibiotics, ed Morin et al., Academic Press, New York., pp. 315–361 (1982); Holden, In: Chemistry and Biology of Beta-Lactam Antibiotics, Vol. 2. Notraditional Beta-Lactam Antibiotics, ed. Morin et al., Academic Press, pp. 101–165 (1982); Koster et al., In: Chemistry and Biology of Beta-Lactam Antibiotics, Vol. 3., the Biology of Beta-Lactam Antibiotics, ed. Morin et al., Academic Press, New York., pp.339–378 (1982); Christensen and Salzmann, In. Handbok of Experimental Pharmacology. Vol. 67/I. Antiobiotics Containing the Beta-Lactam Structure, ed. Demain et al., Springer-Verlag, Berlin, pp. 329–354 (1983); Durckheimer et al. In. Fontiers of Antibiotic Research, ed. Umezawa, Academic Press, Tokyo, pp. 161–192 (1987)).

The chemistry of the formation of 3-amino-2-azetidinones has been reviewed recently (see, Van der Steen and Van Koten, 1992). Beta-lactams of a series of substituted anilines have been prepared, and some of them were found to be competitive inhibitors, but not substrates, of several different types of beta-lactamase enzyme (see, Zrihen et al. Eur. J. Med. Chem.—Chim. Ther. 18:307–314(1983); and Joyeau et al. J. Med. Chem. 31:370–374 (1988)).

The present invention describes a general method for synthesis of compounds of general formula 1. As one of ordinary skill in the art will appreciate, the methods below can be used for a variety of derivatives, and other methods of synthesis are possible. The reaction of a fluorophore precursor having a primary amine that is attached to an aryl carbon with XCH$_2$CH$_2$COX" in the presence of base gives the desired beta-lactam, as shown below:

General synthesis scheme for R$^2$=H

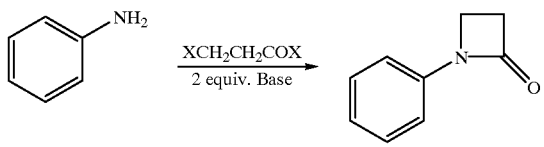

General synthesis scheme for R$^2$=NH$_2$

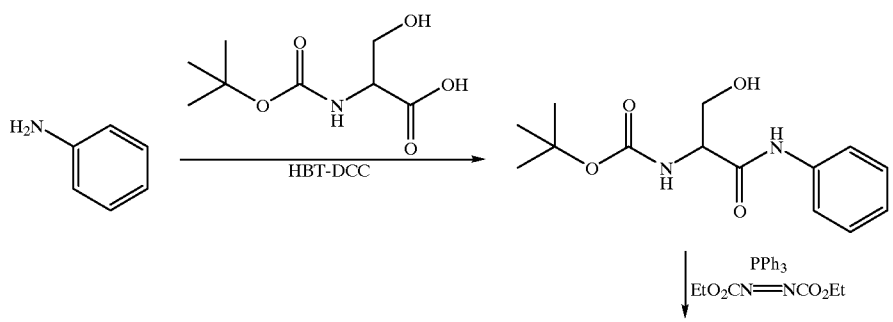

-continued

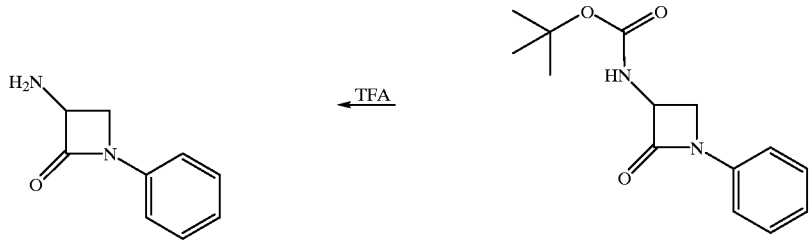

General synthesis scheme for carboxylate containing dyes (the final ester is converted to the free acid in the cytoplasm of the cell).

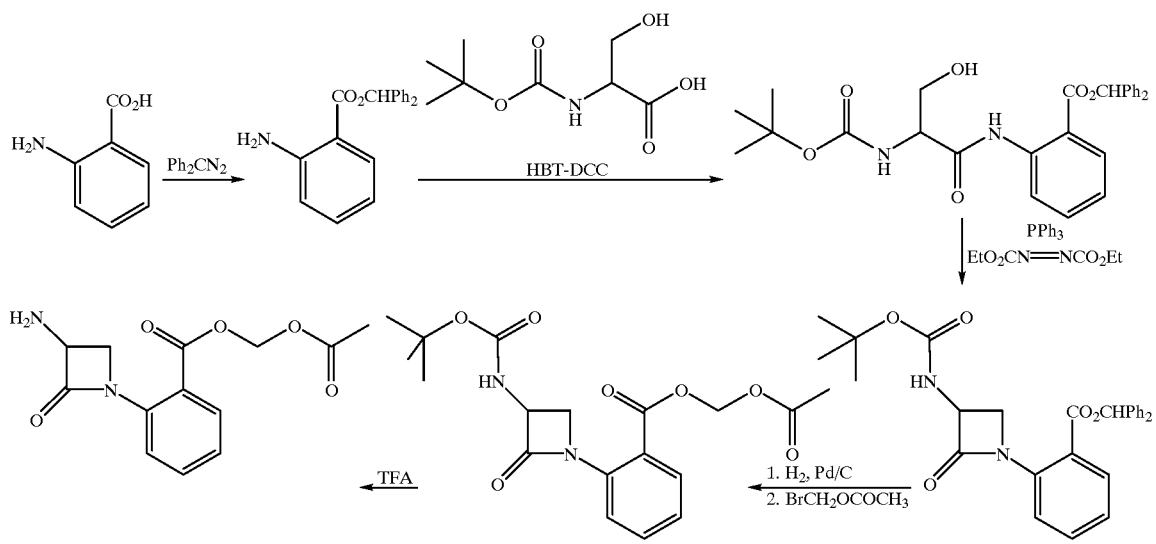

$R^1$ is a moiety, in which a primary amine attached to an aryl carbon of a fluorophore compound is transformed into the nitrogen atom of the beta-lactam ring. In general, any fluorophore precursor can be used in the invention as long as the fluorophore precursor has a primary amine attached to an aryl carbon and the desired fluorescent properties. Preferred fluorophore precursors include aminophthalimide and derivatives of aminophthalimide, aminonaphthalimide and derivatives of aminonaphthalimide, aminophthalic hydrazine and derivatives of aminophthalic hydrazine, fluorescent precursors giving rise to rhodamine rhodol and derivatives thereof, 4-amino-phthalimide and derivatives thereof, 3-amino-phthalimide and derivatives thereof, 3-amino-phthalhydrizide and derivatives thereof, 4-amino-phthalhydrizide and derivatives thereof, anthranilic acid, and 7-amino coumarin and derivatives of 7-amino coumarin. Particularly preferred fluorophore precursors are those fluorophore compounds having formulas 2a–15a (TABLE 1). Many of these fluorophore precursors are commercially available or are readily prepared by a person of ordinary skill in the art.

For $XCH_2CHR^2COX''$, X and X'' are suitable leaving groups. Preferred X is a halogen or a tosylate, and particularly preferred X is Br. Preferred X'' is a halogen, and particularly preferred X'' is Cl. $R^2$ is either H or $-NR^3R^4$, in which $R^3$ and $R^4$ are either H, aliphatic, alkyl, or acyl. Preferred $R^2$ is $-NR^3R^4$. Preferred $R^3$ and $R^4$ groups include H and methyl. Particularly preferred $R^3$ and $R^4$ groups is H. If $R^2$ is $-NR^3R^4$ and not H, then the carbon atom to which $-NR^3R^4$ is bound is chiral and the molecule has two different enantiomers. A mixture having an excess of one enantiomer over the other enantiomer is preferred to an equal mixture of the two enantiomers. If $R^2$ is $-NR^3R^4$ and not H, and the fluorophore precursor has at least one chiral center, then there will be diasteromers. In some cases, it may be necessary to use an excess of $XCH_2CHR^2COX''$ as compared to the fluorophore precursor in the reaction.

The base for the reaction to give compounds having general formula 1 is preferably a base having a basic nitrogen atom, and particularly preferred is pyridine. The reaction conditions (temperature, solvent, reaction time, etc) for the reaction can vary depending on the particular components, and the examples given should give a person of ordinary skill in the art an general idea of what is required.

In general, it is desirable that the compounds of general formula 1 are membrane-permeant by derivatizing them to render them hydrophobic and permeable through cell membranes. Ideally, the derivatizing groups should undergo hydrolysis inside cells to regenerate the compounds of general formula 1 and trap them inside the cells. Therefore, any free amines of the compounds of general formula 1 may be acylated to give an acyl substituent (e.g., acetyl) or converted to various other esters and carbonates (see, Bundgaard, H., Design of Prodrugs, Elsevier Science Publishers (1985), Chapter 1, page 3 et seq.). Likewise, any carboxyls or $-SO_3H$ of the compounds of general formula 1 may be esterified to give, among others, $-O$-alkyl and —O-aliphatic ester substituents. The carboxyl and —SO$_3$H may be esterified with 1-(acyloxy)alkyl, acylthiomethyl, acyloxy-alpha-benzyl, delta-butyrolactonyl, methoxycarbonyloxymethyl, methylsulfinylmethyl, beta-morpholionethyl, 2-(dimethylamino)ethyl, 2-(diethylamino)ethyl, or dialkylaminocarbonyloxymethyl groups as discussed in Ferres, H. (1980) Chem. Ind. 1980: 435–440. A preferred esterifying group for the carboxyl is acetoxymethyl.

Generally, compounds having formula 1 can be made following the general procedures set forth in Examples 1 and 2. Preferred starting materials and products for these reactions are set forth in TABLE 1. When compounds of the general formula 1 (or their membrane permeant derivatives) interact with an appropriate beta-lactamase enzyme, the beta-lactam ring is cleaved, resulting in the product after being cleaved by a beta-lactamase. The resulting cleaved compound can have a carboxyl group that, at physiological pH, will be charged. As a consequence, the cleaved compound will have better intracellular retention than its parent compound.

The starting material, product, and product after being cleaved by a beta-lactamase can be non-fluorescent, short-wavelength fluorescent (meaning, for this purpose, that the excitation and/or emission wavelengths of the product are shorter than those of the starting material) or long-wavelength fluorescent (meaning, for this purpose, that the excitation and/or emission wavelengths of the product are equal to or longer than those of the starting material). Compounds of general formula 1 (and their membrane permeant derivatives) will have different fluorescent properties from their fluorophore precursor. Formation of the beta-lactam ring will shift the fluorescence of the fluorophore precursor to shorter wavelength or even abolishes their fluorescence. Cleavage of the beta-lactam will essentially restore the fluorescence of the fluorophore precursor (with some possible differences that are attributable to the propionic acid moiety that is attached to what was previously a primary amine in the fluorophore precursor).

TABLE 1
| Starting Material | Product | Product After Being Cleaved by a Beta-Lactamase |
|---|---|---|
| 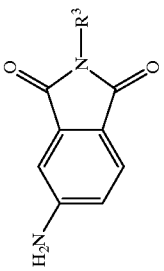 1a | 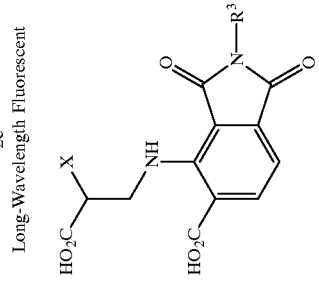 2b Short-Wavelength Fluorescent | 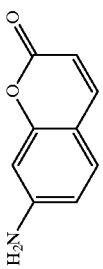 2c Long-Wavelength Fluorescent |
| 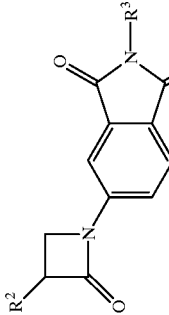 2a | 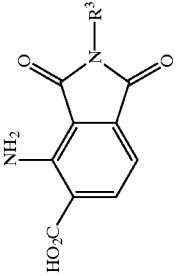 3b Short-Wavelength Fluorescent | 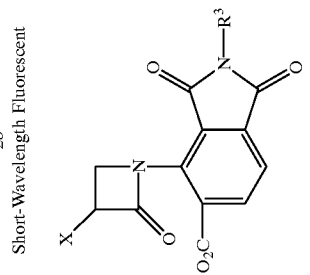 3c Long-Wavelength Fluorescent |
| 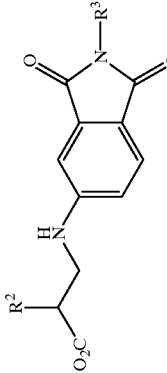 3a | 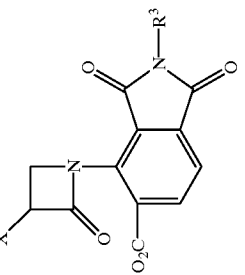 4b Short-Wavelength Fluorescent | 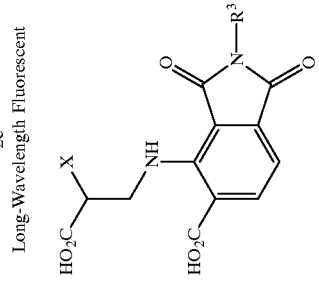 4c Long-Wavelength Fluorescent |

TABLE 1-continued

| Starting Material | Product | Product After Being Cleaved by a Beta-Lactamase |
|---|---|---|
| 5a | 5b Short-Wavelength Fluorescent | 5c Long-Wavelength Fluorescent |
| 6a | 6b Short-Wavelength Fluorescent | 6c Long-Wavelength Fluorescent |
| 7a | 7b Short-Wavelength Fluorescent | 7c Long-Wavelength Fluorescent |

TABLE 1-continued

| Starting Material | Product | Product After Being Cleaved by a Beta-Lactamase |
|---|---|---|
| 8a | 8b Short-Wavelength Fluorescent | 8c Long-Wavelength Fluorescent |
| 9a | 9b Non-Fluorescent | 9c Long-Wave Fluorescent |

TABLE 1-continued
| Starting Material | Product | Product After Being Cleaved by a Beta-Lactamase |
|---|---|---|
| 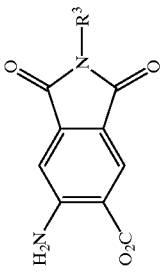 10a | 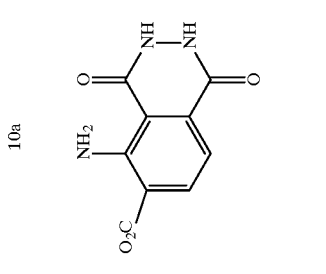 10b Short-Wavelength Fluorescent | 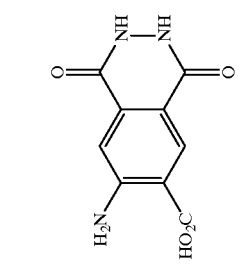 10c Long-Wavelength Fluorescent |
| 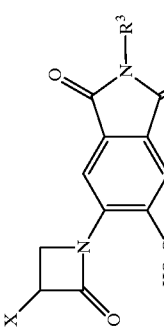 11a | 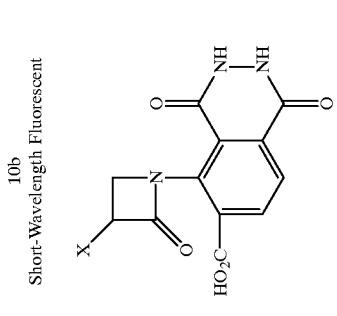 11b Short-Wavelength Fluorescent | 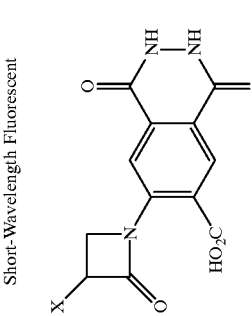 11c Long-Wavelength Fluorescent |
| 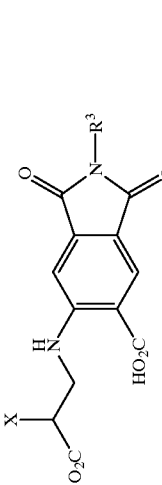 12a | 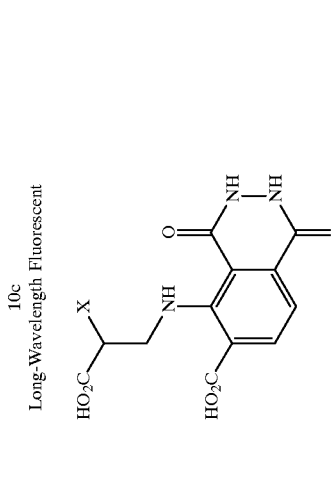 12b Short-Wavelength Fluorescent | 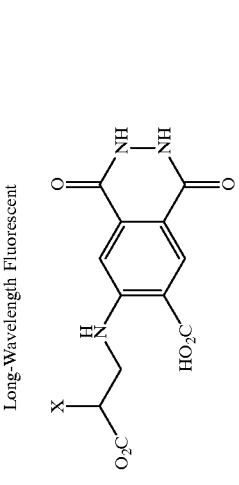 12c Long-Wavelength Fluorescent |

TABLE 1-continued

| Starting Material | Product | Product After Being Cleaved by a Beta-Lactamase |
|---|---|---|
| 13a | 13b Short-Wavelength Fluorescent | 13c Long-Wavelength Fluorescent |
| 14a | 14b Short-Wavelength Fluorescent | 14c Long-Wavelength Fluorescent |
| 15a | 15b Short-Wavelength Fluorescent | 15c Long-Wavelength Fluorescent |

TABLE 1-continued

| Starting Material | Product | Product After Being Cleaved by a Beta-Lactamase |
|---|---|---|
| 16a Non-Fluorescent | 16b Short-Wavelength Fluorescent | 16c Long-Wavelength Fluorescent |
| 17a Non-Fluorescent | 17b Short-Wavelength Fluorescent | 17c Long-Wavelength Fluorescent |

TABLE 1-continued

| Starting Material | Product | Product After Being Cleaved by a Beta-Lactamase |
|---|---|---|
| 17a Non-Fluorescent | 17b Short-Wavelength Fluorescent | 17c Long-Wavelength Fluorescent |
| 18a Non-Fluorescent | 18b Non-Fluorescent | 18c Long-Wave Fluorescent |

TABLE 1-continued

| Starting Material | Product | Product After Being Cleaved by a Beta-Lactamase |
|---|---|---|
| 19a Non-Fluorescent | 19b Short-Wavelength Fluorescent | 19c Long-Wavelength Fluorescent |
| 20a | 20b Short-Wavelength Fluorescent | 20c Long-Wavelength Fluorescent |

TABLE 1-continued
| Starting Material | Product | Product After Being Cleaved by a Beta-Lactamase |
|---|---|---|
| 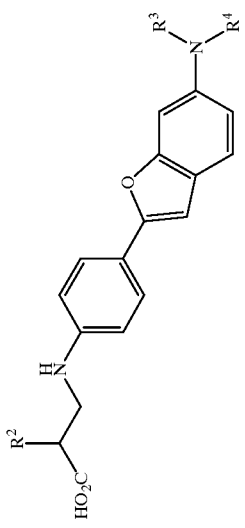<br>21a | 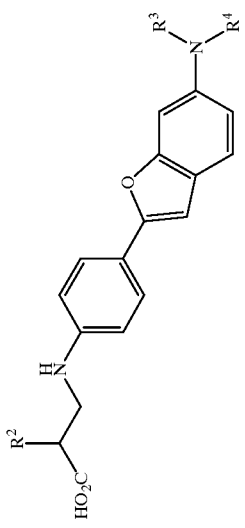<br>21b<br>Short-Wavelength Fluorescent | 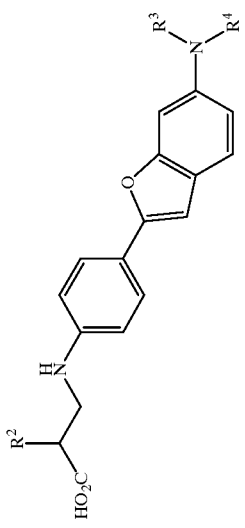<br>21c<br>Long-Wavelength Fluorescent |
| 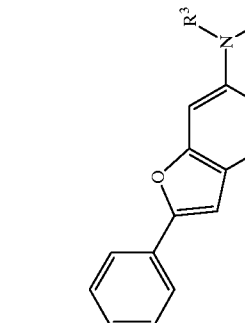<br>22a | 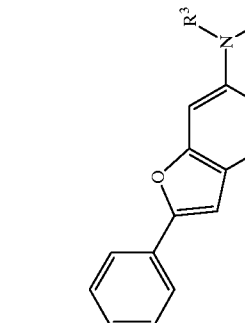<br>22b<br>Short-Wavelength Fluorescent | 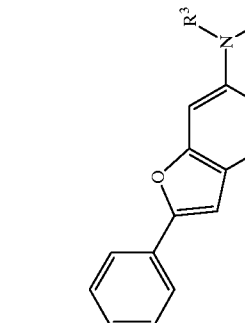<br>22c<br>Long-Wavelength Fluorescent |

TABLE 1-continued

| Starting Material | Product | Product After Being Cleaved by a Beta-Lactamase |
|---|---|---|
| 23a | 23b Short-Wavelength Fluorescent | 23c Long-Wavelength Fluorescent |
| 24a | 24b Short-Wavelength Fluorescent | 24c Long-Wavelength Fluorescent |

TABLE 1-continued

| Starting Material | Product | Product After Being Cleaved by a Beta-Lactamase |
|---|---|---|
| 25a | 25b Short-Wavelength Fluorescent | 25c Long-Wavelength Fluorescent |
| 26a | 26b Short-Wavelength Fluorescent | 26c Long-Wavelength Fluorescent |
| 27a | 27b Short-Wavelength Fluorescent | 27c Long-Wavelength Fluorescent |

TABLE 1-continued

| Starting Material | Product | Product After Being Cleaved by a Beta-Lactamase |
|---|---|---|
| 28a | 28b Short-Wavelength Fluorescent | 28c Long-Wavelength Fluorescent |
| 29a | 29b Short-Wavelength Fluorescent | 29c Long-Wavelength Fluorescent |

As used in this table, $R^3$ and $R^4$ are as defined herein, and are preferably independently selected from the group consisting of H, lower alkyl, or $CH_2(CH_2)nOCO(CH_2)nCH_3$, wherein n is 0 or an integer from 1 to 10, inclusive, preferably 1 to 5, inclusive. As used in this table, "short-wavelength fluorescent" and "long-wavelength fluorescent" reflect the relative fluorescence of the compounds in a given row.

Beta-lactamase Enzymes

Beta-lactamase enzymes are a class of enzymes that have been characterized because of their clinical relevance in making bacteria resistant to beta-lactam antibiotics (see, Waley, S. G., Sci. Prog. 72: 579–597 (1988); Richmond, M. H. et al., Ann. N.Y. Acad. Sci. 182: 243–257 (1971)). Many beta-lactamases have been cloned and their amino acid sequence determined (see, Ambler, R. P., Phil. Trans. R. Soc. Lond. (Ser.B.) 289: 321–331 (1980)).

A large number of beta-lactamase enzymes have been isolated and characterized, all of which may be suitable for use in accordance with the present invention. Initially, beta-lactamase enzymes were divided into different classes (I through V) on the basis of their substrate and inhibitor profiles and their molecular weight (see, Richmond, M. H. and Sykes, R. B., Adv.Microb.Physiol. 9: 31–88 (1973)). More recently, a classification system based on amino acid and nucleotide sequence has been introduced (see, Ambler, R. P., Phil. Trans. R. Soc. Lond. (Ser.B.) 289: 321 –331 (1980)). Class A beta-lactamases possess a serine in the active site and have an approximate weight of 29 kd. This class contains the plasmid-mediated TEM beta-lactamases such as the RTEM enzyme of pBR322. Class B beta-lactamases have an active-site zinc bound to a cysteine residue. Class C enzymes have an active site serine and a molecular weight of approximately 39 kd, but have no amino acid homology to the class A enzymes.

The coding region of an exemplary beta-lactamase that could be employed in the reporter gene assays has been described and is available in pTG2del1 (see, Kadonaga J. T. et al., J.Biol.Chem. 259: 2149–2154 (1984)). The entire coding sequence of wild-type pBR322 beta-lactamase has also been published (see, Sutcliffe, J. G., Proc.Natl.Acad.Sci.USA 75: 3737–3741 (1978)). As would be readily apparent to those skilled in the field, this and other comparable sequences for peptides having beta-lactamase activity would be equally suitable for use in accordance with the present invention. The beta-lactamase reporter gene is employed in an assay system in a manner well known per se for the use of reporter genes (for example, in the form of a suitable plasmid vector).

In addition, mutants of these beta-lactamase sequences can be prepared that may have a different specificity, i.e., mutants may cleave compounds of general formula 1 (or their membrane permeant derivatives) that a naturally occurring beta-lactamase enzymes may not. Techniques for mutagenesis are well known in the art (Sambrook et al., Molecular Cloning, A Laboratory Manual, Cold Spring Harbor Laboratory Press (1989)). Numerous studies of site directed mutagenesis have been completed on beta-lactamase (Sigal et al. J. Biol. Chem. 259:5327–5332 (1984); Dalbadies-McFarland et al. Biochemistry 25:332–338 (1986); Schultz and Richards, Proc. Natl. Acad. Sci. USA 83:1588–1592 (1986); Madgwick et al., Biochem. J. 248:657–662 (1987); Ellerby et al. Biochemistry 29:5797–5806 (1990); Gibson et al. Biochem. J. 272:613–619 (1990); Jacob et al. Biochem. J. 271 :399–406 (1990); Lenfant et al. Biochimie 72:495–503 (1990); Adachi et al. J. biol. Chem. 266:3186–3191 (1991); Escobar et al. Biochemistry 30:10783–10787 (1991); Jacob-Dubuisson et al. Protein Eng. 4:811–819 (1991); Juteau et al. Biotechniques 11:460–462 (1991); Lenfant et al. J. Biol. Chem. 266:17187–17194 (1991); Delaire et al. J. Biol. Chem. 267:20600–20606 (1992); Juteau et al. Prot. Eng. 5:693–701 (1992); Lamotte-Brasseur et al. Biochem. J. 282:189–195 (1992); Thornewell and Waley, Biochem. J. 288:1045–1051 (1992); Zafaralla et al. Biochemistry 31:3874–3852 (1992); Knox et al. Protein Eng. 6:11–18 (1993); Lenfant et al. Eur. J. Biochem. 217:939–946 (1993)).

In addition, some single point mutations created functional enzymes with drastically altered substrate specificities (see, Collatz et al. Gene 78:349–354 (1989); Palzkill and Botstei, J. Bacteriol. 5237–5243 (1992); Jacob et al. Protein Eng. 4:79–86 (1990); Sowek et al. Biochemistry 30:3179–3188 (1991); Delaire et al. Protein Eng. 4:805–810 (1991); Healey et al. Proteins 6:275–283 (1989); Lee et al. Proteins 11:45–51 (1991)).

A variety of random mutagenesis techniques have also been used to mutate beat-lactamase enzymes (see, Oliphant and Struhl, Proc. Natl. Acad. Sci. USA 86:9094–9089 (1989); Shortle et al. Proc. Natl. Acad. Sci. USA 77:5375–5379 (1980); Dalbadie-McFarland et al. Proc. Natl. Acad. Sci. USA 79:6409–6413 (1982); Shortle and Botstein, Basic. Life Sci. 20:147–155 (1982); Dalbadie-McFarland et al. Biochem. Soc. Trans. 12:226–228 (1984); Barany, Proc. Natl. Acad. Sci. USA 82:4202–4206 (1985); Barany, Gene 37:111–123 (1985); Kadonaga and Knowles, Nucleic Acids Res. 13:1733–1745 (1985); Foster et al. J. Bacteriol. 169:2476–2481 (1987); Anthony-Cahill et al. Trends Biochem. Sci. 14:400–403 (1989); Zebala and Barany, Gene 100:51–57 (1991); Palzkill and Botstein, Proteins 14:29–44 (1992)).

Assays

The compounds of general formula 1 (or their membrane permeant derivatives) have advantages over other types of fluorescent compounds in reporter gene assays. Most notably, this invention does not rely on fluorescent resonant energy transfer (FRET) between a donor and acceptor molecule in the assay (for FRET, see, WO 96/30540, to Tsien, published Oct. 3, 1996). Because quenching between a donor and acceptor molecule is rarely entirely complete, gene reporter systems that use FRET have background signals that may reduce the sensitivity of their assays. In contrast, the compounds of general formula 1 (or their membrane permeant derivatives), when used in a reporter gene assay, have negligible background. The compounds of general formula 1 (or their membrane permeant derivatives) fluoresce upon excitation with light of the proper wavelength only if a beta-lactamase enzyme has cleaved the beta-lactam ring. Because of the reduced background signal, the compounds of general formula 1 (or their membrane permeant derivatives) may give a more sensitive reporter gene assay.

The interaction of a particular compound of general formula 1 (or its membrane-permeant derivative) with a particular beta-lactamase enzyme can be readily determined. The method involves contacting the sample with a compound having general formula 1 (or its membrane-permeant derivative), exciting at one or more wavelengths that are suitable for the cleaved compound, and determining the degree of fluorescence in the sample. A degree of fluorescence that is greater than an expected amount indicates that the particular beta-lactamase enzyme can cleave the particular compound having the general formula 1 (or its membrane-permeant derivative). The amount of fluorescence expected can be determined using, for example, a control sample, or control values determined contemporaneously, prior to, or after a particular assay was performed. Such expected values can include a statistical analysis, such as a mean and standard deviation, to provide a chosen statistical confidence level. Both naturally occurring beta-lactamase enzymes and beta-lactamase enzymes prepared by mutagenesis can be tested with a particular compound having the general formula 1 (or its membrane-permeant derivative). A particular compound having the general formula 1 (or its membrane permeant derivative) is a substrate for the particular beta-lactamase enzyme that cleaved the beta-lactam ring.

Even if a particular compound of general formula 1 (or its membrane-permeant derivative) is not cleaved by a naturally occurring beta-lactamase enzyme, the particular compound of general formula 1 or membrane-permeant derivative may have value as an inhibitor of the naturally-occurring beta-lactamase enzyme. The ability of a compound to inhibit a beta-lactamase can be confirmed using methods set forth in the present invention. For example, samples comprising beta-lactamase activity can be contacted with a compound of the present invention, and further contacted with a substrate for beta-lactamase. An amount of beta-lactamase activity less than expected indicates that the compound inhibits beta-lactamase activity. The expected level of activity can be determined using a proper control or historical values, or other methods known in the art.

The assay systems of the present invention provide an advantageous and rapid method of isolation and clonal selection of stably transfected cell lines containing reporter genes and having the desired properties which the transfection was intended to confer, e.g. fluorescent signal response after activation of a transfected receptor with a high signal-to-noise ratio from a high proportion of isolated cells. Current procedures for clonal selection of satisfactorily transfected, genetically engineered cells from the initial population, are done mainly by replica plating of colonies, testing of one set of colonies, visual selection of preferred clones manual isolation of the replicas of the preferred clones by pipetting, and prolonged cellular cultivations. This procedure is laborious and time-consuming, and it may require several months to generate a clone useful for assays suited to drug screening. Moreover, it is difficult to manually select and maintain more than a few hundred clones.

Using the assays of this present invention, the desired signal from cellular beta-lactamase reporter system can be maintained within living and viable cells. Replica plating of colonies can be unnecessary because single cells cam be assayed and remain viable for later culturing and expansion. Thus, from a population of initially transfected cells, an artisan can rapidly select those few individual living cells with the best fluorescent signal using automated instruments such as a fluorescent-activated cell sorter (e.g. the Becton Dickinson FACS Vantage™). The selected cells can then be collected for culturing and expansion to produce a clonal cell line with the desired properties for assays and drug screening.

As would be immediately apparent to those working in the field, the combination of a substrate of this invention and a suitable beta-lactamase enzyme can be used in a wide variety of different assay systems (see, U.S. Pat. No. 4,740, 459). In particular, the substrates of the invention can enable the detection of beta-lactamase activity in a wide variety of biologically important environments, such as human blood serum, the cytoplasm of cells and intracellular compartments, which can facilitate the measurement of periplasmic or secreted beta-lactamase enzyme.

Further, the expression of any target protein may be detected by fusing a gene encoding the target protein to a beta-lactamase gene, which can be localized by immunostaining or fluorescence or electron microscopy. For example, beta-lactamase fusion proteins can be detected in the lumen of organelles through the use of the substrates of the invention. In this instance, only subcellular compartments containing the fusion protein fluoresce at a wavelength characteristic of the cleaved substrate, whereas all others fluoresce at a wavelength characteristic of the intact molecule.

Both the intact and cleaved substrate can be efficiently retained in cells without the use of special measures, such as chilling. The change in fluorescence of the compound caused by cleavage by a beta-lactamase (even in individual small mammalian cells) can be visible through a fluorescence microscope using normal color vision or photographic film. In addition, the fluorescence signal can be quantified and further enhanced by conventional digital image processing techniques.

Monitoring Gene Expression

The compounds of general formula 1 (or their membrane permeant derivatives) may make it feasible to use beta-lactamase as a reporter gene to monitor the expression of a protein from a set of expression control sequences. In one aspect, this invention provides methods for monitoring gene expression from a set of expression control sequences by using beta-lactamase as a reporter gene.

Recombinant Nucleic Acids

As used herein, the term "nucleic acid molecule" includes both DNA and RNA molecules. It will be understood that when a nucleic acid molecule is said to have a DNA sequence, this also includes RNA molecules having the corresponding RNA sequence in which "U" replaces "T." The term "recombinant nucleic acid molecule" refers to a nucleic acid molecule which is not naturally occurring, and which comprises two nucleotide sequences which are not naturally joined together. Recombinant nucleic acid molecules are produced by artificial combination, e.g., genetic engineering techniques or chemical synthesis.

Nucleic acids encoding beta-lactamases can be obtained by methods known in the art, for example, by polymerase chain reaction of cDNA using primers based on the DNA sequence of a beta-lactamase (for PCR methods, see U.S. Pat. No. 4,683,195; Mullis et al. (1987) Cold Spring Harbor Symp. Quant. Biol. 51:263; and Erlich, ed., PCR Technology, (Stockton Press, N.Y., 1989). In addition, beta-lactamase enzymes can be prepared by mutagenesis using methods known in the art to produce variants of wild-type beta-lactamases.

The construction of expression vectors and the expression of genes in transfected cells uses molecular cloning techniques known in the art (see, Sambrook et al., Molecular Cloning—A Laboratory Manual, Cold Spring Harbor Laboratory, Cold Spring Harbor, N.Y., (1989); and Current Protocols in Molecular Biology, F. M. Ausubel et al., eds., (Current Protocols, a joint venture between Greene Publishing Associates, Inc. and John Wiley & Sons, Inc., ). The choice of the parent expression vector is one within the skill of the artisan based on known factors, such as the organism into which the expression vector is to be placed. The insertion of nucleic acid sequences encoding beta-lactamase activity into the expression vector in an appropriate orientation is also known in the art, as is the ability to insert such sequences into particular locations within the vector.

Nucleic acids used to transfect cells with sequences coding for expression of a polypeptide of interest generally will be in the form of an expression vector including expression control sequences operatively linked to a nucleotide sequence coding for expression of the polypeptide. As used, the term nucleotide sequence "coding for expression of" a polypeptide refers to a sequence that, upon transcription and translation of mRNA, produces the polypeptide. As any person skilled in the are recognizes, this includes all degenerate nucleic acid sequences encoding the same amino acid sequence. This can include sequences containing, e.g., introns.

As used herein, the term "expression control sequences" refers to nucleic acid sequences that regulate the expression of a nucleic acid sequence to which it is operatively linked. Expression control sequences are "operatively linked" to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons.

The recombinant nucleic acid can be incorporated into an expression vector comprising expression control sequences. These expression control sequences can be operativley linked to the recombinant nucleic acids, which can encode a beta-lactamase activity. The expression vector can be adapted for function in prokaryotes or eukaryotes by inclusion of appropriate promoters, replication sequences, markers, codons, and the like as is known in the art.

This invention provides novel recombinant nucleic acid molecules including expression control sequences adapted for function in a mammalian or non-mammalian eukaryotic cell operably linked to a nucleotide sequence coding for the expression of a cytosolic beta-lactamase enzyme. As used herein, "cytosolic beta-lactamase enzyme" refers to a beta-lactamase enzyme that lacks amino acid sequences for secretion from the cell membrane (e.g., the signal sequence). This invention provides recombinant nucleic acid molecules including expression control sequences adapted for function in a mammalian or non-mammalian eukaryotic cell operably linked to a nucleotide sequence coding for the expression of a beta-lactamase enzyme.

It is preferable that the ribosome binding site and nucleotide sequence coding for expression of a beta-lactamase enzyme contain sequences preferred by the host cells, such as eukaryotic and mammalian cells. Such sequences improve expression of beta-lactamase in mammalian cells. Preferred sequences for expression in mammalian cells are described in, for example, Kozak, M., J. (Cell Biol. 108: 229–241 (1989)), which are referred to herein as "Kozak sequences."

When used in mammalian cells, the expression control sequences are adapted for function in mammalian cells. The method of this invention is useful to testing expression from any desired set of expression control sequences. In particular, this invention is useful for testing expression from inducible expression control sequences, such as those regulated by signal transduction. As used herein, "inducible expression control sequences" refers to expression control sequences that respond to biochemical signals either by increasing or decreasing the expression of sequences to which they are operably linked. For example, in the case of genes induced by steroid hormones, the expression control sequences includes hormone response elements. The binding of a steroid hormone receptor to the response element induces transcription of the gene operably linked to these expression control sequences. Expression control sequences for many genes, and for inducible genes in particular, have been isolated and are well known in the art. The invention also is useful with control sequences that control the constitutive expression of regulated proteins.

The transfected cell may be incubated under conditions to be tested for expression of a beta-lactamase enzyme from the expression control sequences. The cell or an extract of the cell is contacted with a substrate of this invention under selected test conditions and for a period of time to allow catalysis of the substrate by any beta-lactamase enzyme expressed. Then the cleaved substrate is excited with radiation of an appropriate wavelength, and the fluorescence emitted measured. If the cell did not express a beta-lactamase enzyme, very little of the substrate will have been cleaved, and there will be little fluorescence attributable to the cleaved compound. If the cell expressed a large amount of a beta-lactamase enzyme, most of the substrate will be cleaved, and there will be a great deal of fluorescence attributable to the cleaved substrate. In one aspect, this method can be used to compare mutant cells to identify which cells possess greater or less enzymatic activity. Such cells can be sorted using, for example, a fluorescent cell sorter based on fluorescence.

As will be apparent to those working in the field of reporter gene cell-based assays for screening samples or pools of samples (such as compounds (combinatorial or synthetic), natural products or extracts thereof, or marine animal extracts) to identify potential drug candidates which act as agonists, inverse agonists, or antagonists of cellular signaling or activation, the combination of cells (preferably mammalian) genetically engineered to express a beta-lactamase enzyme under the control of different regulatory elements/promoters and the use of the substrates of this invention may provide distinct advantages over known reporter genes (including, but not limited to, chloramphenicol acetyl transferase, firefly luciferase, bacterial luciferase, Vargula luciferase, aequorin, beta-galactosidase, alkaline phosphatase) and their requisite substrates.

By choosing appropriate regulatory elements and promoters to control expression of a beta-lactamase enzyme, assays may be constructed to detect or measure the ability of test substances to evoke or inhibit functional responses of intracellular hormone receptors. These include expression control sequences responsive to inducible by mineralcorticosteroids, including dexanethasone (see, J. Steroid Biochem. Molec. Biol. Vol. 49, No. 1 1994, pp.31–3), gluococorticoid, and thyroid hormone receptors (see, U.S. Pat. No. 5,071,773). Additional intracellular receptors include retinoids, vitamin D3 and vitamin A (see, Leukemia vol 8, Suppl. 3, 1994 ppS1-–S10; Nature Vol. 374, 1995, p.118–119; and Seminars in Cell Biol., Vol. 5, 1994, p.95–103). Specificity of expression of the beta-lactamase can be accomplished by using the appropriate promoter/enhancer element. Additionally, by choice of other regulatory elements or specific promoters, drugs that influence expression of specific genes can be identified. Such drugs could act on specific signaling molecules such as kinases, transcription factors, or molecules such signal transducers and activators of transcription (see, Science Vol. 264, 1994, p.1415–1421; and Mol. Cell Biol., Vol. 16, 1996, p.369–375). Specific microbial, parasitic or viral promoters or other regulatory sequences that are potential drug targets can also be assayed in such test systems.

Also by choosing promoters such as c-fos or c-jun (see, U.S. Pat. No. 5,436,128; and Proc. Natl. Acad. Sci. Vol. 88, 1991, pp. 5665–5669) or promoter constructs containing regulatory elements responsive to second messengers (see, Oncogene, 6: 745–751 (1991) (including cyclic AMP-responsive elements, phorbol ester response element (responsive to protein kinase C activation), serum response element (responsive to protein kinase C-dependent and independent pathways) and Nuclear Factor of Activated T-cells response element (responsive to calcium) to control expression of beta-lactamase enzyme, assays may be constructed to detect or measure substances or mixtures of substances that modulate cell-surface receptors including, but not limited to, the following classes: receptors of the cytokine superfamily such as erthyropoietin, growth hormone, interferons, and interleukins (other than IL-8) and colony-stimulating factors; G-protein coupled receptors (see, U.S. Pat. No. 5,436,128) for hormones, such as calcitonin, epinephrine or gastrin, pancrine or autocrine mediators, such as stomatostatin or prostaglandins, and neurotransmitters such as norepinephrine, doparnine, serotonin or acetylcholine; tyrosine kinase receptors such as insulin growth factor, nerve growth factor (U.S. Pat. No. 5,436,128). Furthermore, assays may be constructed to identify substances that modulate the activity of voltage-gated or ligand-gated ion channels, modulation of which alters the cellular concentration of second messengers, particularly calcium (see, U.S. Pat. No. 5,436,128). Assays can be constructed using cells that intrinsically express the promoter, receptor or ion channel of interest or into which the appropriate protein has been genetically engineered.

The expression control sequences can also be those responsive to substances that modulate cell-surface receptors or that modulate intracellular receptors. To determine whether a substance or mixture of substances activates extracellular or intracellular receptors or other cellular responses, cells containing a beta-lactamase enzyme controlled by a desired promoter/enhancer element can be incubated with at least one test substance. A compound of this invention is then added, and after a period of time has passed, the fluorescence emission of the cleaved substrate is measured. This result is compared to fluorescent emissions from control samples that have had no drug treatment and, when feasible, control samples with a known inhibitor and a known activator. The effect of any active drugs may then be determined using the ratio of the fluorescence signal found in test wells to the signals found in wells with no drug treatment.

Assays are performed in wells in a microtiter plate containing 96 or more wells, or in an assay system with no compartments, such as a gel matrix or moist membrane environment. Detection can be performed for example by microtiter plate fluorimeters, e.g. Millipore Cytofluor®, or imaging devices capable of analyzing one or more wells or one or more assay points in a certain surface area (e.g. as supplied by Astro-med West Warwick, R.I.). Furthermore, the fluorescent signal from the cleaved substrate can be detected in single cells, which allows assay miniaturization and an increased number of tests per surface area. Miniaturized assays also further increase the throughput of an imaging detection system because there are more samples within the imaging field.

The assay systems of the present invention may further provide an advantageous and rapid method of isolation and clonal selection of stably transfected cell lines containing reporter genes and having the desired properties which the transfection was intended to confer, e.g. fluorescent signal response after activation of a transfected receptor from a high proportion of isolated cells. Current procedures for clonal selection of satisfactorily transfected, genetically engineered cells from the population initial transfected with the vectors of interest, are done mainly by manual means and involve several rounds of microscopic analyses, selecting the visually preferred clone, isolation of the clone by manual pipetting stages and prolonged cellular cultivations This procedure is laborious and time-consuming; it may require several months to generate a clone useful for assays suited to drug screening. Moreover, it is difficult to manually select and maintain more than a few hundred clones. Using the assays of this present invention, the desired signal from cellular beta-lactamase reporter system may be maintained within living and viable cells. Thus, one may rapidly select, from the population of initially transfected cells, those few living cells with the best fluorescent signal using automated instruments such as a fluorescent-activated cell sorter, e.g. the Becton Dickinson FACS Vantage. The selected cells may then be collected for cultivation and propagation to produce a clonal cell line with the desired properties for assays and drug screening.

In addition, the presence (for example, in human serum, pus, urine, or other fluid, sample, or tissue) of bacteria resistant to beta-lactam antibiotics may be readily detected by using the substrates of this invention. Only in the presence of an active beta-lactamase enzyme is there a fluorescence spectrum that is characteristic of the cleaved compound.

The invention may be better understood with reference to the accompanying examples, which are intended for purposes of illustration only and should not be construed as in any sense limiting the scope of the invention as defined in the claims appended hereto.

EXAMPLES

Procedures

All silica gel chromatography was performed using silica gel (Merck, grade 60, 230–400 mesh, 60 micrometers) purchased from Aldrich (Milwaukee, Wis.). Bakerbond Octadecyl from J. T. Baker was used for C18 reverse phase chromatography. Solvents (high pressure liquid chromatography grade) were used for chromatography as received, or dried over activated molecular sieves (3 micrometers) for synthetic purposes.

Methods of performing assays on fluorescent materials are well known in the art and are described (see, e.g., Lakowicz, J. R., Principles of Fluorescence Spectroscopy, New York: Plenum Press (1983); Herman, B., Resonance energy transfer microscopy, in: Fluorescence Microscopy of Living Cells in Culture, Part B, Methods in Cell Biology, vol. 30, ed. Taylor, D. L. & Wang, Y.-L., San Diego: Academic Press (1989), pp. 219–243; Turro, N. J., Modern Molecular Photochemistry, Menlo Park: Benjamin/Cummings Publishing Col, Inc. (1978), pp. 296–361).

Fluorescence excitation and emission spectra will be measured either on a Spex Fluorolog 111 or on a K2 fluorometer (ISS, Champaigne, Ill.) with a rhodamine B quantum counter. For fluorescence microscopy imaging, two different imaging setups will be used. One, with an inverted fluorescence microscope, Zeiss IM-35 (Thornwood, N.Y.) coupled to a silicon-intensified target (SIT) camera (Dage-MTI, Michigan City, Ind.) has been described in detail (see, Tsien, R. Y. (1986) New tetracarboxylate chelators for fluorescence measurement and photochemical manipulation of cytosolic free calcium concentrations, in: Optical Methods in Cell Physiology, ed. de Weer, P. & Salzberg, B., New York:Wiley, pp. 327–345; Tsien and Harootunian (1990) Cell Calcium 11:93–109). The other consisted of a cooled charge-coupled-device (CCD) camera (Photometrics, Tucson, Ariz.) connected to an inverted fluorescence microscope (Zeiss Axiovert).

Example 1

Preparation of 4-methyl-7-(2-oxoazetidinyl)-2H-chromogen-2-one

The reaction of fluorophore precursor 7-amino-4-methyl-2H-chromen-2-one (Aldrich) with $BrCH_2CH_2C(O)Cl$ in pyridine produced 4-methyl-7-(2-oxoazetidinyl)-2H-chromogen-2-one. Briefly, 180 mg (1.0 mmol) of 7-amino-4-methylcoumarin was stirred with 1 ml of pyridine in 5 ml of chloroform to which 115 µl (1.0 mmol) of 3-bromopropionyl chloride in 1 ml of chloroform were added dropwise on ice. The solution was warmed to 40° C. for thirty minutes, after which another equivalent of 3-bromophropionyl chloride was added. This solution was kept at 40° C. overnight. Tem milliliters of methylene chloride were poured into the solution and the solution was extracted twice with equal volumes of half saturated aqueous sodium bicarbonate solution, twice with one volume of dilute aqueous hydrochloric acid, and once with water. The organic layer was dried over anhydrous sodium sulfate and the solvent removed in vacuo. The residue was dissolved in hot methanol from which the product, 4-methyl-7-(2-oxoazetidinyl)-2H-chromogen-2-one, crystallized in colorless crystals upon cooling. The product was characterized as follows: $^1H$ NMR ($CDCl_3$): δ2.44 ppm (s, 3H, methyl), δ2.91 ppm, 3.04 ppm (2dd, 2H, $J_1 \approx J_2=6.4$ Hz, beta-lactam C-4), δ3.74 ppm, 3.91 ppm (2dd, 2H, $J_1 \approx J_2=6.4$ Hz, beta-lactam C-3), δ6.23 ppm (s, 1H, coumarin C-3), δ7.57 ppm (d, 1H, J=8.7 Hz, coumarin), δ7.65 ppm (d, 1H, J=1.9 Hz, coumarin), δ7.75 ppm (dd, 1H, $J_1$=8.7 Hz, $J_2$=1.9 Hz, coumarin).

Example 2

Preparation of 7-(3-amino-2-oxoazetidinyl)-4-methyl-2H-chromen-2-one

Briefly, 1.1 mmol N-BOC-L-Serine (Fluka) is dissolved in 2 ml methylene chloride. Then 1.1 mmol 7-Amino-4-methylcoumarin and 1.2 mmol hydroxybenztriazole are added with stirring. Over a period of 30 minutes, a solution of 1.3 mmol dicyclohexyl carbodiimide in 1.4 ml methylene chloride is added dropwise. The reaction is stirred at room temperature for 20 hours, during which time a precipitate of dicyclohexylurea forms. The precipitate is removed by filtration and washed with methylene chloride. The combined solutions (filtrates) are evaporated under reduced pressure and the residue chromatographed over silica gel with methylene chloride—ethylacetate as the eluent yielding 2-((tert-butoxy)carbonylamino)-3-hydroxy-N-(4-methyl-2-oxo(2H-chromen-7-yl))propanamide.

This product and 1.5 equivalents of triphenylphosphine are dissolved in 3.5 ml tetrahydrofuran and chilled on ice to 0° C. Over one hour, 1.5 equivalents of diethylazodicarboxylate are added dropwise to the chilled solution. The reaction is allowed to warm to room temperature and stirred for 15 hours. The solvents are removed in vacuo at 35° C. and the resulting gum chromatographed over silica with ethylene chloride—ethylacetate as the eluent yielding (tert-butoxy)-N-(3-(4-methyl-2-oxo)2H-chromen-7-yl))-2-oxo(3-azetidinyl))fornamide.

This product is treated with 1 ml trifluoroacetic acid at room temperature for 15 minutes. The liquids are removed in vacuo at 35° C. and the product, (7-(3-amino-2-oxoazetidinyl)-4-methyl-2H-chromen-2-one), is purified by silica gel chromatography with mehanol-chloroform as the eluent.

Example 3

Preparation of 9-(3-amino-2-oxoazetidinyl)spiro[1,3,4,6,11-pentahydro-1,11-dioxanaphthacence-6,3'-2'oxaindane]-2,19-dione Briefly, 0.4 g (1 mmol) 2-(6-amino-2-(2-carboxyethyl)-3-oxoxanthen-9-yl)benzoic acid was dissolved in 1 ml hot acetic acid and added to 20 ml of dry nitrobenzene at 120° C. Over 2 hours, the reaction temperature was raised to 210° C. The solution was cooled to 120° C. and the solvent removed at approximately 18 kPa (house vacuum line, 135 Torr) to leave 0.5 ml of solution. Chloroform (0.5 ml) was added and the solution poured onto a short silica column. Nitrobenzene was removed by elution with hexane. The product, 9-aminospiro[1,3,4,6,11-pentahydro-1,11-dioxanaphtacene-6,3'-2'-oxaindane]-2,19-dione, was collected with ethyl acetate-hexane (2:1). Yield of title compound as an orange solid was 0.26 g (0.67 mmol, 67%) and was characterized as follows: $^1H$ NMR ($CDCl_3$): δ2.74 ppm (m, 2H, methylene), δ2.82 ppm (m, 2H, methylene),δ6.36 ppm (m, 1H, xanthene), δ6.54 ppm (s, 1 H, xanthene), δ6.56 (m, 1H, xanthene), δ6.59 ppm (s, 1H, xanthene), δ6.97 ppm (s, 1H, xanthene), δ7.18ppm (m, 1H, phthalic), δ7.66 ppm (m, 2H, phthalic), δ8.04 ppm (m, 1H, phthalic).

Next, 1.1 mmol N-BOC-L-Serine is dissolved in 2 ml methylene chloride. 1.1 mmol of the above product and 1.2 mmol hydroxybenztriazole are added with stirring. Over a period of 30 minutes a solution of 1.3 mmol dicyclohexyl carbodiimide in 1.4 ml methylene chloride is added dropwise. The reaction is stirred at room temperature for 20 hours during which a precipitate of dicyclohexylurea forms. The precipitate is removed by filtration and washed with methylene chloride. The combined solutions are evaporated under reduced pressure and the residue chromatographed over silica gel with methylene chloride—ethylacetate as the eluent yielding 2-((tert-butoxy)carbonylamino)-N-(1,18-dioxospiro[2'-oxaindane-3,5'-5,7,8,10,12-pentahydro-10,12-dioxanaphthacene]-3-hydroxypropanamide.

The above product and 1.5 equivalents of triphenylphosphine are dissolved in 3.5 ml tetrahydrofuran and chilled on ice to 0° C. Over one hour, 1.5 equivalents diethylazodicarboxylate are added dropwise to the chilled solution. The reaction is let warm to room temperature and stirred for 15 hours. The solvents are removed in vacuo at 35° C. and the resulting gum chromatographed over silica with ethylene chloride—ethylacetate as the eluent to provide the product (tert-butyoxy)-N-3-(1,18-dioxospiro[2'-oxaindane-3,5'-5,7,8,10,12-pentahydro-10,12-dioxanaphthacene]-11-yl)-2-oxo(3-azetidinyl))formamide.

This product is treated with 1 ml trifluoroacetic acid at room temperature for 15 minutes. The liquids are removed in vaccuo at 35° C. and the product purified by silica gel chromatography with mehanol-chloroforrn as the eluent yielding 9-(3-amino-2-oxoazetidinyl)spiro[1,2,4,6,11-pentahydro-1,11-dioxanaphthacene-6,3'-2'-oxaindane]-2,19-dione.

The present invention provides compounds for beta-lactamase enzymes. While specific examples have been provided, the above description is illustrative and not restrictive. Many variations of the invention will become apparent to those skilled in the art upon review of this specification. The scope of the invention should, therefore, be determined

We claim:

1. A compound of the formula:

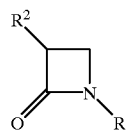

wherein:
- $R^1$ is a moiety, in which a primary amine attached to an aryl carbon of a fluorophore precursor was converted into the nitrogen atom of the beta-lactam ring and the fluorophore precursor is not anthralic acid or a meta or para amino benzoic acid when $R^2$ is H;
- $R^2$ is selected from the group consisting of H and $-NR^3R^4$, in which $R^3$ and $R^4$ are selected from the group consisting of H, aliphatic, alkyl, and acyl.

2. The compound of claim 1, wherein the fluorophore precursor is 7-amino coumarin or a derivative of 7-amino coumarin and the beta-lactam ring may be cleaved by a beta-lactamase enzyme.

3. The compound of claim 2, wherein the compound is 4-methyl-7-(2-oxoazetidinyl)-2H-chromen-2-one.

4. The compound of claim 2 of the formula 2b.

5. The compound of claim 1, wherein the fluorophore precursor is aminophthalimide or a derivative of aminophthalimide.

6. The compound of claim 5 of the formula 3b.

7. The compound of claim 5 of the formula 4b.

8. The compound of claim 1 of the formula 5b.

9. The compound of claim 1, wherein the fluorophore precursor is aminophthalic hydrazide or a derivative of aminophthalic hydrazide.

10. The compound of claim 9 of the formula 6b.

11. The compound of claim 1, wherein the fluorophore precursor is aminonaphthalimide or a derivative of aminonaphthalimide.

12. The compound of claim 11 of the formula 7b.

13. The compound of claim 11 of the formula 8b.

14. The compound of claim 1 of the formula 9b.

15. The compound of claim 1, wherein the compound of claim 1 is a membrane-permeant derivative.

16. The compound of claim 1, wherein said compound is located within a living cell.

17. A method for determining whether a compound of claim 1 is a substrate for a beta-lactamase enzyme, comprising: contacting said compound with a sample containing said beta-lactamase enzyme; exciting at the wavelength for the said compound when cleaved; and measuring fluorescence.

18. The method of claim 17, wherein said compound is a membrane permeant derivative.

19. The method of claim 17, wherein said beta-lactamase enzyme has been prepared by mutagenesis of another beta-lactamase enzyme.

20. A method for detecting the presence of beta-lactamase activity in a sample, comprising:

contacting the sample with at least one compound of general formula 1

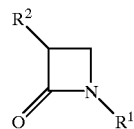

wherein:
- $R^1$ is a moiety, in which a primary amine attached to an aryl carbon of a fluorophore precursor was converted into the nitrogen atom of the beta-lactam ring and the fluorophore precursor is not anthralic acid when $R^2$ is H;
- $R^2$ is selected from the group consisting of H and $-NR^3R^4$, in which $R^3$ and $R^4$ are selected from the group consisting of H, aliphatic, alkyl, and acyl; and
- the beta-lactam ring may be cleaved by a beta-lactamase enzyme.

21. The method of claim 20, wherein said sample has a beta-lactamase reporter gene.

22. The method of claim 21, wherein said beta-lactamase reporter gene is in a mammalian cell.

23. The method of claim 20, wherein samples having beta-lactamase activity are separated from samples having no beta-lactamase activity by fluorescent-activated cell sorting.

24. The method of claim 20, wherein the beta-lactamase activity results from a beta-lactamase enzyme that was prepared by mutagenesis of another beta-lactamase enzyme.

25. The method of claim 20, wherein said compound is a membrane permeant derivative.

26. The method of claim 20, wherein said fluorophore precursor is selected from the group consisting of the method of preparation of claim 13, wherein the fluorophore precursor is selected from the group consisting of 7-amino coumarin and derivatives of 7-amino coumarin, aminophthalimide and derivatives of aminophthalimide, aminophthalic hydrazide and derivatives of aminophthalic hydrazide, or aminonaphthalimide and derivatives of aminonaphthalimide.

27. The method of claim 20, wherein $R^2$ is $NR^3R^4$, wherein $R^3$ and $R^4$ are H.

* * * * *

UNITED STATES PATENT AND TRADEMARK OFFICE
CERTIFICATE OF CORRECTION

PATENT NO.    : 6,031,094
DATED         : February 29, 2000
INVENTOR(S)   : Roger Y. Tsien et al.

It is certified that error appears in the above-identified patent and that said Letters Patent is hereby corrected as shown below:

Column 45,
In the formula, please replace "R" with -- $R^1$ --.

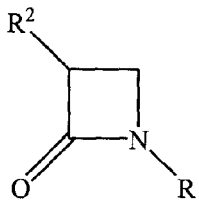

Signed and Sealed this

Twenty-ninth Day of November, 2005

JON W. DUDAS
*Director of the United States Patent and Trademark Office*